United States Patent [19]

Sauers

[11] 4,043,794

[45] Aug. 23, 1977

[54] N-PHOSPHONOCARBONYL CARBAMIC ACID DERIVATIVES AS PLANT GROWTH REGULANTS

[75] Inventor: Richard Frank Sauers, Hockessin, Del.

[73] Assignee: E. I. Du Pont de Nemours and Company, Wilmington, Del.

[21] Appl. No.: 688,930

[22] Filed: May 21, 1976

[51] Int. Cl.$^2$ .......................... A01N 9/36; C07F 9/40

[52] U.S. Cl. ....................................... 71/86; 260/935; 260/938; 260/943

[58] Field of Search ............................ 71/86; 260/935

[56] References Cited

U.S. PATENT DOCUMENTS

| | | | |
|---|---|---|---|
| 3,627,507 | 12/1971 | Langsdorf, Jr. | 71/76 |
| 3,849,102 | 11/1974 | Bucha et al. | 71/86 X |
| 3,861,898 | 1/1975 | Jelinek | 71/86 X |
| 3,929,448 | 12/1975 | Brantley | 71/86 X |

FOREIGN PATENT DOCUMENTS

| | | |
|---|---|---|
| 1,042,208 | 9/1966 | United Kingdom |

*Primary Examiner*—Joseph Paul Brust

[57] ABSTRACT

This invention relates to the use of carbonyl phosphonates for retarding the growth of plants, especially woody plants and agricultural compositions containing such phosphonates.

4 Claims, No Drawings

N-PHOSPHONOCARBONYL CARBAMIC ACID DERIVATIVES AS PLANT GROWTH REGULANTS

BACKGROUND OF THE INVENTION

This invention relates to compounds which are useful for retarding the growth rate of plants and in particular woody plants. Many instances exist wherein it is desirable to control the growth rate of plants and yet not destroy them. In particular, it is desirable to control the growth of plants which are in the vicinity of power lines and railroad rights-of-way.

Previous discoveries in this area include the following U.S. patents.

U.S.Pat. No. 3,627,507 discloses the use of phosphonates of Formula (a) for retarding the growth rate of woody vegetation:

(a)

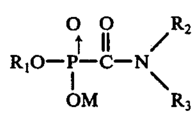

where $R_2$ and $R_3$ can be the same or different and each can be H, $C_1$–$C_4$ alkyl, $C_3$–$C_4$ alkenyl or alkynyl, or $R_2$ and $R_3$ can be taken together to form a ring.

U.S. Pat. No. 3,849,102 discloses the growth retardant use of the compounds of Formula (b)

(b)

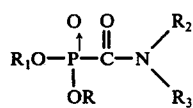

where

R and $R_1$ are alkyl or substituted alkyl and $R_2$ and $R_3$ are as defined for Formula (a).

British Pat. Specification No. 1,042,208 discloses the use of compounds of Formula (c) for the preparation of lubricating compositions:

(c)

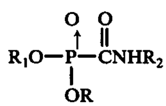

where

R and $R_1$ are alkyl or substituted alkyl and $R_2$ is an acyl group, optionally substituted with one or more chlorine atoms.

Also, V. A. Shokol, B. N. Kozhushko, and A. V. Kirsanov in the Journal of General Chemistry (USSR) Vol. 43, page 547 (1973) disclose the preparation of a compound of Formula (c) where R and $R_1$ are $CH_3CH_2O$— and $R_2$ is $$CH_3CH_2OOC(=O)—.$$

No use for this compound is disclosed.

Since there is a need for growth retarding compounds, research has continued in this area.

SUMMARY OF THE INVENTION

According to this invention, it has been discovered that certain carbonyl phosphonates have outstanding growth-retarding ability. The growth retarding carbonyl phsophonates of the instant invention are to be found in Formula I:

Formula I

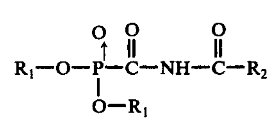

where $R_1$ is methyl or ethyl; and $R_2$ is methyl, ethyl, methoxy, or ethoxy, said methyl or ethyl groups optionally substituted with 1 to 3 chlorine atoms.

Preferred for reasons of higher growth retardant activity, or ease and/or economy of synthesis, are those compounds of Formula I where, independently;

a. $R_2$ is methoxy or ethoxy; or b. $R_2$ is methyl or ethyl, substituted with 1 to 3 chlorine atoms.

Specifically preferred for its highest activity is:

Methyl N-(Dimethoxyphosphonocarbonyl)carbamate, m.p. 68°–70° C.

DETAILED DESCRIPTION OF THE INVENTION

I

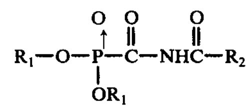

Compounds of Formula I can be formed by reaction of a dialkyl phosphite and an appropriate isocyanate in an inert solvent such as benzene, methylene chloride, or chloroform containing a catalytic quantity of a trialkyl amine. Compounds of Formula I are useful growth retardants and also serve as valuable intermediates for preparation of the salts of Formula II.

Compounds of Formula II where M is sodium, lithium, or potassium, are formed by reaction of Formula I compounds where $R_1$= alkyl with sodium, lithium, or potassium iodide in an inert solvent in which the iodide salt is appropriately soluble.

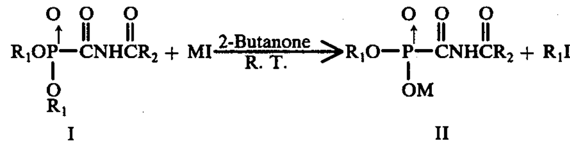

Examples of such solvents are tetrahydrofuran, p-dioxane, acetone, and 2-butanone. The ammonium and alkyl ammonium salts of Formula II are obtained by passage of a solution containing the sodium, lithium or potassium salts through an ion exchange column previously treated with the appropriate ammonium cation.

The isocyanates which are precursors to the compounds of this invention can be prepared by reaction of the corresponding amide with oxalyl chloride [A. J. Speziale, L. R. Smith, and J. E. Fedder, J. Org. Chem. 30, 4306 (1965)]. Acetyl and propionyl isocyanate are, however, more easily prepared by reaction of acetyl or propinyl chloride with isocyanic acid in the presence of pyridine as described in U.S. Pat. No. 3,155,700.

The following Examples further illustrate the preparation of the compounds of this invention. In these examples all parts are by weight and temperatures and are reported in degrees centigrade unless otherwise indicated.

EXAMPLE 1

To a solution of 11.0 parts of diethylphosphite in 175 parts of methylene chloride and 4 drops of triethyl amine was added 10.0 parts of ethoxycarbonyl isocyanate. The solution was refluxed for 3 hours. Removing the solvent under reduced pressure left 18.5 parts of colorless oil which partially crystallized. The crystals were washed with cyclohexane to give 7.3 parts of ethyl N-(diethylphosphonocarbonyl)carbamate, m.p. 57°-64°, The proton nmr spectrum was consistent with this structure. ($\delta NH = 10.0$ ppm)

EXAMPLE 2

A solution of 2.75 parts of dimethyl phosphite, 4.70 parts of trichloroacetyl isocyanate and 4 crystals of 1,4-diazabicyclo[2.2.2]octane in 100 parts of benzene was refluxed for 4 hours. The solvent was removed under reduced pressure and the residue heated to 100° C at 0.1 mm Hg. pressure to remove unreacted dimethylphosphite. The resulting yield of dimethyl [(trichloroacetyl)aminocarbonyl]-phosphonate was 6.3 parts as a viscous oil. The infrared spectrum was consistent with this structure ($\gamma C{=}O = 1780\ cm^{-1}$)

In a similar fashion, using the appropriate dialkyl phosphite and isocyanate, the following compounds of Formula I can also be prepared:

| $R_1$ | $R_2$ | mp |
|---|---|---|
| $CH_3$— | $CH_3O$— | 68-70° |
| $CH_3$— | $CH_3CH_2O$— | |
| $CH_3$— | $CHCl_2$— | |
| $CH_3$— | $CH_2Cl$— | |
| $CH_3$— | $CH_3$— | |
| $CH_3$— | $CH_3CCl_2$— | |
| $CH_3CH_2$ | $CH_3O$— | |
| $CH_3CH_2$— | $CCl_3$— | |
| $CH_3CH_2$— | $CHCl_2$— | |
| $CH_3CH_2$— | $CH_2CCl$— | |
| $CH_3CH_2$— | $CH_3$— | |
| $CH_3CH_2$— | $CH_3CCl_2$— | |
| $CH_3CH_2$— | $CH_3CH_2$— | |

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 1% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable and Water Soluble Powders | 20-90 | 0-74 | 0.5-10 |
| Dusts | 1-25 | 70-99 | 0-5 |
| Granules and Pellets | 1-95 | 5-99 | 0-15 |
| High Strength Compositions | 90-99 | 0-10 | 0-2 |
| Aerosols | 1-10 | 80-98 | 1-10 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. Additionally, common salts urea and sugar are particularly suitable for water soluble powders. The more absorptive diluents are preferred for wettable powders and the denser ones for dusts. In many cases, water is an excellent solvent. Other typical liquid diluents and solvents are described in Marsden, "Solvent Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", The Manufacturing Confectioner's Publ. Co., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). For procedures to make dispensible granulated or pelleted products, see J. E. Browning, "Agglomeration", *Chemical Engineering*, Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example: W. P. Langsdorf, U.S. Pat. No. 3,846,512, Nov. 5, 1974, columns 12 through 21; G. C. Klingman, "Weed Control as a Science", John Wiley & Sons, Inc., New York, 1961, pp. 81-96; and J. D. Fryer and S. A. Evans, "Weed Control Handbook", 5th Edn. Blackwell Scientific Publications, Oxford, 1968, pp. 101-103.

EXAMPLE 3

A wettable powder having the following composition is prepared:

| | |
|---|---|
| methyl N-(dimethoxyphosphono-carbonyl)carbamate | 25% |
| sodium alkylnaphthalenesulfonate | 1% |
| sodium ligninsulfonate | 1% |
| attapulgite | 73% |

The ingredients are blended and ground in a hammer mill to pass a U.S.S. No. 50 screen (0.3 mm openings). All compounds of the invention can be formed in a similar fashion.

EXAMPLE 4

The following aerosol preparation is prepared:

| | | |
|---|---|---|
| A | methyl N-(dimethoxyphosphono-carbonyl)carbamate | 2% |
| | water | 28% |
| B | asphalt | 20% |
| | xylene | 25% |
| | polyglycerol stearate | 5% |
| C | dichloro difluoromethane | 20% |

The preformed aqueous phase (A) comprising active ingredient in water, is combined with the organic phase (B), comprising a solution of asphalt, emulsifier and xylene, with agitation. To this is added, in an aerosol container under pressure, the propellant (C).

UTILITY

The compounds of the present invention are useful as plant growth regulants. More particularly, the compounds of the present invention are useful for controlling the growth of woody and herbaceous plants.

The compounds of the present invention are effective in different stages of plant growth and may, in general, be applied as circumstances dictate. For example, they may be applied in the spring to actively-growing vegetation with the result that further growth is controlled or completely arrested. They may be applied in the fall with the result that growth the following spring will be controlled or completely arrested. Thus, these compounds have utility in a wide variety of industrial and agricultural applications, including, but not restricted to, control of vegetation situated along power line rights of way that if unattended would grow up to the locus of the power lines.

The precise amount of the compounds of the present invention to be used will vary according to the particular plant species to be controlled, the method of application, climate, etc. Broadly speaking, they may be used at rates of about 0.25 to 25 kilograms per hectare, preferably about two to 12 kilograms per hectare.

The plant growth retardant activity of the compounds of the present invention was discovered in greenhouse tests, as explained below:

PROCEDURE, TEST 1

Seeds of crabgrass (Digitaria, spp.), barnyardgrass (*Echinochloa crusgalli*), wild oats (*Avena fatua*). *Cassia tora*, morningglory (Impomoea spp.), cocklebur (Xanthium spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the second trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three–five leaves were sprayed. Treated plants and controls were maintained in a greenhouse for sixteen days, then all species were compared to controls and visually rated for response to treatment.

Ratings for compounds tested by this procedure are recorded in Table 1.

TABLE I

| COMPOUND | LB. PER ACRE | POST EMERGENCE | | | | | | | | | | | | | |
|---|---|---|---|---|---|---|---|---|---|---|---|---|---|---|---|
| | | BUSH BEAN | COTTON | MORN-ING GLORY | COCK-LEBUR | CASSIA | NUT-SEDGE | CRAB-GRASS | BARN-YARD GRASS | WILD OATS | WHEAT | CORN | SOY-BEAN | RICE | SOR-GHUM |
| $CH_3O-\overset{O}{\overset{\parallel}{\underset{CH_3O}{\underset{\mid}{P}}}}-\overset{O}{\overset{\parallel}{C}}-NH-\overset{O}{\overset{\parallel}{C}}OCH_3$ | 2 | 5G | 2H 8G | 9G | 3G | 2G | 0 | 0 | 1C | 0 | 0 | 5G | 2G | 0 | 2C 7G |
| $CH_3O-\overset{O}{\overset{\parallel}{\underset{OCH_3}{\underset{\mid}{P}}}}-\overset{O}{\overset{\parallel}{C}}-NH-\overset{O}{\overset{\parallel}{C}}-CCl_3$ | 2 | 2H 8G 6Y | 1C 8G | 3G | 5G | 0 | 0 | 4H | 3H | 0 | 5G | 2U 6G | 1H 6G | 3G | 2C 7G |

| PRE-EMERGENCE | | | | | | | | | | | |
|---|---|---|---|---|---|---|---|---|---|---|---|
| MORN-ING GLORY | COCK-LEBUR | CASSIA | NUT-SEDGE | CRAB-GRASS | BARN-YARD GRASS | WILD OATS | WHEAT | CORN | SOY-BEAN | RICE | SOR-GHUM |
| 0 | 0 | 0 | 0 | 0 | 0 | 0 | 0 | 0 | 0 | 0 | 0 |
| 0 | 2H | 3C | 0 | 6H | 9H | 3G | 8G 5I | 2H 7G | 6H | 10E | 2H |

The plant response ratings (above) are composed of a number and a letter. The number describes the extent of the response (one exception is "6Y" explained below) and ranges from zero to ten with zero representing no response, and ten representing 100% response. The letter describes the type of the response, with C representing chlorosisnecrosis, E emergence inhibited, G growth retarded, H formative effect (malformation or hormone type), I increased chlorophyll, U unusual pigmentation (other than dark green color) and X axillary stimulation (leaf/bud ratio changed on broadleaves; tillering on grasses). As mentioned above, 6Y is an exception and represents abscised buds or flowers (without regard to the extent of this effect).

An additional greenhouse test was conducted, as described below:

PROCEDURE, TEST 2

The test compounds were applied in a nonphytotoxic solvent with a wetting agent and a humectant as overall sprays on pots of privet (Ligustrum sp.), willow (Salix sp), Forsythia (Forsythia sp.), loblally pine (*Pinus Taeda*), and apple (Malus sp.). The plants were maintained in a greenhouse. Plant response ratings were taken one week and eight weeks after application, and appear in Table 2.

TABLE 2

(TEST 2)

| COMPOUND | Rate kg/ha | Privet 1 wk. | Privet 8 wk. | Willow 1 wk. | Willow 8 wk. | Forsythia 1 wk. | Forsythia 8 wk. | Loblolly Pine 1 wk. | Loblolly Pine 8 wk. | Apple 1 wk. | Apple 8 wk. |
|---|---|---|---|---|---|---|---|---|---|---|---|
| $CH_3O-P(=O)(OCH_3)-C(=O)-NH-C(=O)OCH_3$ | 1 | 0 | 6G | 0 | 0 | 0 | 9G | 0 | 0 | 0 | 0 |
| | 2 | 0 | 9G | 0 | 0 | 0 | 10G | 0 | 0 | 0 | 6G 3X |
| | 4 | 0 | 10G | 0 | 9G | 0 | — | 0 | 8C | 0 | 9G 5X |
| | 8 | 0 | 10G | 5P | 9G 7D | 0 | 10G SI | 0 | 10C | 9C | 10C |

The plant response ratings (above) are derived in the same fashion as in Table 1. D represents defoliation, P represents terminal bud injury, and a dash indicates that the particular species wasn't included in the test, or wasn't considered ratable because of technical difficulties.

What is claimed is:

1. A method for retarding the growth of plants which comprises applying a growth regulating amount of a compound of the formula:

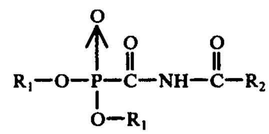

where $R_1$ is methyl or ethyl; and $R_2$ is methyl, ethyl, methoxy, or ethoxy, said methyl or ethyl groups optionally substituted with 1 to 3 chlorine atoms.

2. The method of claim 1 wherein $R_2$ is methoxy or ethoxy.

3. The method of claim 1 wherein $R_2$ is methyl or ethyl, substituted with 1 to 3 chlorine atoms.

4. The method of claim 1 wherein the compound is methyl N-(dimethoxyphosphonocarbonyl)carbamate.

* * * * *